United States Patent

Tamura et al.

[11] Patent Number: 5,840,650
[45] Date of Patent: Nov. 24, 1998

[54] PROCESS OF MAKING A CATALYST FOR PRODUCING OXIRANE COMPOUNDS

[75] Inventors: Mitsuhisa Tamura; Kazuhiro Yamauchi; Kenshi Uchida, all of Ichihara, Japan

[73] Assignee: Sumitomo Chemical Company, Limited, Osaka, Japan

[21] Appl. No.: 622,171

[22] Filed: Mar. 27, 1996

[30] Foreign Application Priority Data

Mar. 30, 1995 [JP] Japan .................................. 7-073319

[51] Int. Cl.$^6$ ........................................... B01J 21/00
[52] U.S. Cl. ..................... 502/350; 502/349; 502/407; 502/240; 502/242
[58] Field of Search ..................... 502/349, 350, 502/407, 240, 242

[56] References Cited

U.S. PATENT DOCUMENTS

| | | | |
|---|---|---|---|
| 3,923,843 | 12/1975 | Wulff .............................. | 260/348.5 L |
| 4,018,816 | 4/1977 | Onoda et al. ..................... | 260/486 R |
| 4,367,342 | 1/1983 | Wulff et al. ..................... | 549/529 |
| 4,424,320 | 1/1984 | McDaniel .......................... | 502/236 |
| 4,499,209 | 2/1985 | Hoek et al. ...................... | 518/707 |
| 4,520,124 | 5/1985 | Abe et al. ........................ | 502/159 |
| 4,596,786 | 6/1986 | Kukes et al. ..................... | 502/643 |
| 5,466,835 | 11/1995 | Nemeth et al. ................... | 549/531 |

FOREIGN PATENT DOCUMENTS

| | | |
|---|---|---|
| 0 345 856 | 12/1989 | European Pat. Off. . |
| 2 704 159 | 10/1994 | France . |
| WO 94/23834 | 10/1994 | WIPO . |

*Primary Examiner*—Hien Tran
*Assistant Examiner*—Nadine Preisch
*Attorney, Agent, or Firm*—Sughrue, Mion, Zinn, Macpeak & Seas, PLLC

[57] ABSTRACT

A heterogeneous catalyst used for producing an oxirane compound by reacting an olefinic compound with an organic hydroperoxide which catalyst is substantially insoluble in the reaction mixture, comprises at least one silicon compound, selected from the group consisting of silica and inorganic silicates, in chemical combination with an oxide or hydroxide of titanium, and is obtained by a process comprising the steps of (a) impregnating the silicon compound with a titanium compound in a solvent for impregnation, (b) removing the solvent for impregnation (c) then washing the remaining composition with a washing solvent and removing the washing solvent, and (d) then calcining the residual composition.

6 Claims, No Drawings

PROCESS OF MAKING A CATALYST FOR PRODUCING OXIRANE COMPOUNDS

BACKGROUND OF THE INVENTION

The present invention relates to a catalyst used for producing oxirane compounds and a process for producing oxirane compounds using the catalyst.

It is already known in the art to react an olefinic compound with an organic hydroperoxide with the aid of a heterogeneous catalyst comprising at least one silicon compound, selected from the group consisting of solid silica and inorganic silicates, in chemical combination with an oxide or hydroxide of titanium, to convert the olefinic compound into an oxirane compound (JP-B-56-35941, 54-40525, 54-40526 and 50-30049).

The heterogenous catalyst comprising solid silica and/or inorganic silicate and titanium chemically bonded thereto can be prepared by various known methods. For example, a method is known which comprises impregnating the silicon compound with a titanium compound in a solvent, then removing the solvent and calcining the remaining composition. However, the catalyst prepared by the above-mentioned method is unsatisfactory in both activity and selectivity. In commercial scale production, when the activity of the catalyst is low, excessively large reactors are necessary; when the selectivity is low and the amount of by-products is large, excessively large purification facilities are necessary and the energy necessary for purification is high, resulting in a high production cost. Accordingly, development of a catalyst which is excellent both in activity and in selectivity has been eagerly desired.

The present inventors have made extensive study to develop a catalyst which can be used in producing oxirane compounds with excellent activity and excellent selectivity. As the result, it has been found that a catalyst prepared by a process which, in addition to the process steps of the above-mentioned known method for preparing a catalyst, subsequently to the step of removing the solvent used for impregnation, further comprises the steps of washing the mixture with a washing solvent and then removing the washing solvent exhibits both excellent activity and excellent selectivity when used in producing oxirane compounds. The present invention has been accomplished on the basis of above finding.

SUMMARY OF THE INVENTION

According to the present invention, there are provided a heterogeneous catalyst used for producing an oxirane compound by reacting an olefinic compound with an organic hydroperoxide which catalyst is substantially insoluble in the reaction mixture, comprises at least one silicon compound, selected from the group consisting of solid silica and inorganic silicates, in chemical combination with an oxide or hydroxide of titanium, and is obtained by a process comprising the steps of:

(a) impregnating the silicon compound with a titanium compound in a solvent for impregnation,
(b) removing the solvent for impregnation,
(c) then washing the remaining composition with a washing solvent and removing the washing solvent, and
(d) then calcining the residual composition; and a process for producing an oxirane compound by reacting an olefinic compound with an organic hydroperoxide in the presence of the said catalyst.

DETAILED DESCRIPTION OF THE INVENTION

In catalytic reactions, in general, an important condition for attaining high activity and high selectivity is to prepare uniform catalytically active sites. In the present reaction, it is generally thought that the titanium chemically bonded to solid silica and/or inorganic silicate constitutes the catalytically active sites. In the above-mentioned known method, after impregnation, after merely removing the solvent used for impregnation, the next step of calcining is conducted. In this method, accordingly, the composition proceeds to the step of calcining while still containing residual titanium compound not chemically bonded to the solid silica and/or inorganic silicate. The remaining titanium compound not bonded chemically is considered to be converted into titania having low activity and low selectivity by calcining. It is considered that, as the result, the active sites of chemically bonded titanium and titania having low activity and low selectivity come to exist together in the product, resulting in a catalyst of lowered activity and selectivity. The present inventors have made extensive study based on the idea of making the amount of remaining titanium compound not bonded chemically as small as possible, and resultantly found that a catalyst which shows excellent reaction results can be obtained, after impregnating a silicon compound with a titanium compound and then removing the solvent used for impregnation, by further washing the remaining composition with a washing solvent, then removing the washing solvent, followed by calcining. As compared with catalysts obtained by the prior method which comprises no washing step, the catalyst of the present invention is excellent both in activity and in selectivity.

The catalyst of the present invention contains titanium chemically bonded to solid silica and/or inorganic silicate, and the titanium is considered to be present in the tetravalent state. Further, it is considered that the titanium is bonded to the solid silica and/or inorganic silicate in the form of an oxide, for example,

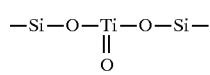

The solid silica and/or inorganic silicates used in the present invention contain preferably at least 50%, more preferably at least 75%, most preferably at least 90%, in the form of its dioxide, of silicon. The solid silica and/or inorganic silicates preferably have a relatively large specific surface area. The specific surface area is preferably at least 1 m$^2$/g, more preferably 25–800 m$^2$/g.

The silica is preferably synthetic porous silica of a relatively high density and of close pack type which is composed of amorphous silica particles coagulated or bound to one another, and may be, for example, silica gel, precipitated silica, or the like. The method of preparation of such synthetic silica and its properties are described in "The Colloid Chemistry of Silica and Silicates", (written by R. G. Iler, pub. by Cornell University Press, New York, U.S.A., 1955, Chapter VI) and U.S. Pat. No. 2,657,149. Among the silica gels available on the market, those which have a specific surface area of 25–700 m$^2$/g, pore volume of 0.3–2.0 ml/g and silica content of at least 99% by weight are preferably used. Silica powders consisting of particles of amorphous silica flocculated in open-packed, readily disintegrated, loosely knit aggregates may also be favorably used. An example of such silica is fumed pyrogenic silica obtained by subjecting hydrogen and oxygen together with silicon tetrachloride or silicon tetrafluoride to combustion operation. Various silicas of this kind are available on the market, which include, for example, Cab-o-sil (a registered trade mark, mfd. by Cabot Corporation) and Aerosil (a registered trade mark, mfd. by Degussa). Particularly preferred among these silica products are those which have a specific surface area of 50–500 m²/g and silica content of at least 99%.

Crystalline aluminosilicates known as molecular sieves may also be used as the solid silica and/or inorganic silicates. Naturally occurring crystalline silicates may also be used, examples of which include asbestos minerals, such as serpentine (hydrous magnesium silicate), clay minerals, such as hectorite (lithium magnesium silicate), kaolin and bentonite, and mica minerals, such as phlogopite (aluminum magnesium potassium silicate) and vermiculite (hydrous magnesium silicate).

Among these kinds of silica and silicates described above, synthetic amorphous solid silica and/or inorganic silicates are preferably used, and those which consist substantially of pure silica and have a silica content of, for example, at least 95% are particularly preferably used.

The solvents used for impregnation and washing may be oxygen containing organic solvents which have 1 to about 12 carbon atoms and are liquid at ordinary temperature. They are, for examples, alcohols, ketones, ethers (both acyclic and cyclic) and esters. Specific examples thereof include alcohols, such as methanol, ethanol, ethylene glycol, propylene glycol, isopropanol, n-butanol and octanol; ketones, such as acetone, diethyl ketone, methyl ethyl ketone and methyl isobutyl ketone; hydrocarbon ethers, such as diisobutyl ether and tetrahydrofuran, and hydrocarbon esters, such as methyl acetate, ethyl acetate, butyl acetate and butyl propionate.

Though the solvent for impregnation and the washing solvent may be the same or different, preferably used as the washing solvent are above-mentioned alcohols.

The titanium compounds used in the present invention may be soluble titanium salts of inorganic acids or organic acids and titanic acid esters. Specific examples of the titanium compounds include tetramethyl titanate, tetraethyl titanate, tetrapropyl titanate, tetraisopropyl titanate, tetrabutyl titanate, tetraisobutyl titanate, tetra-2-ethylhexyl titanate, tetraoctadecyl titanate, titanium tetrachloride, titanium tetrabromide, titanium tetraiodide, titanium (IV) oxyacetylacetonate, and titanium (IV) diisopropoxide bisacetylacetonate. When alcohols or ketones are used as the solvent for impregnation, titanium tetrachloride and lower titanic acid esters are preferably used.

The impregnation solution preferably has a titanium concentration of about 0.01 mol/l to about 1.0 mol/l. Specific examples of the solution include an alcohol solution of titanium tetrachloride and a solution of a titanic acid ester having 1–10 carbon atoms per alkoxy group in an alcohol having 1–10 carbon atoms. The concentration of the titanium compound in the impregnation solution and the amount of the solution used are preferably adjusted so as to give a titanium content in the ultimate catalyst in the range of about 0.1 to about 10% by weight, as calculated in terms of the titanium amount relative to the weight of the inorganic siliceous solid substance, a titanium content of 1.5% by weight or less being more preferred. A low titanium content results in improved activity and improved selectivity. In order to give the desired titanium content and desired activity, a multi-stage impregnation process which either goes or does not go through a drying and/or calcining step also may be used.

The catalyst of the present invention may contain a small amount of a catalyst modifier. Examples of the catalyst modifier include alkali metals, such as lithium, sodium, potassium and rubidium, and alkaline earth metals, such as magnesium, calcium, strontium and barium. These modifiers are added in a soluble form to the impregnation solution. In general, suitably 5% by weight (as metals) or less of the catalyst modifier is added to the present catalyst. It is advisable to add about 0.25–1.0% by weight of such a catalyst modifier as sodium, potassium, calcium and magnesium.

Subsequently to the impregnation, the solvent absorbed in the siliceous substance is removed. The solvent removal operation may contain decantation, filtration, centrifugal separation, evacuation, drying and other suitable operations. The conditions in the solvent removal step are so selected that preferably 80%, more preferably 90%, of the excess of liquid organic solvent used for impregnation might be removed.

After removal of the solvent, washing is conducted. The washing solvent and the catalyst from which the solvent for impregnation has been removed are thoroughly mixed, and the liquid phase portion is separated by such means as filtration or decantation. This operation is repeated a necessary number of times. Completion of washing can be judged, for example, by the analysis of the liquid phase portion. The washing temperature is preferably 0°–100° C., more preferably 10°–60° C. After completion of the washing, the remaining washing liquid is removed by the same technique as used in the step of removing the solvent for impregnation. The solvent removal is useful for recovering a large amount of solvent and, at the same time, for reducing the danger of inflammation during calcining and further, for preventing the lowering of physical strength of the catalyst caused by abrupt vaporization of large amount of volatile solvent which might occur in the catalyst structure during the subsequent, higher-temperature calcining. Drying at 25° C.–200° C., subsequent to decantation, is effective as a means of solvent removal and is preferable.

After the step of washing and removal of the washing solvent, the catalyst composition is calcined.

The atmosphere for calcining is, for example, a non-reductive gas, such as nitrogen, argon and carbon dioxide, and an oxygen-containing gas, such as air. One role of the calcining is to convert titanium from the form supported on the solid siliceous substance, namely the form of halide, alkoxide, etc., into an insoluble, chemically bonded oxide. The other role of the calcining is to activate the catalyst. The calcining temperature is preferably 400° C.–900° C., more preferably 400° C.–700° C. The period of time of calcining is preferably about 1–18 hours.

The catalyst thus obtained is preferably contacted with a silylating agent before use. The silylating agent may be, for example, an organic silane, organic silylamine, organic silylamide and its derivatives, organic silazane, and other silylating agent. Specific examples of organic silanes include chlorotrimethylsilane, dichlorodimethylsilane, chlorobromodimethylsilane, nitrotrimethylsilane, chlorotriethylsilane, iododimethylbutylsilane, chlorodimethylphenylsilane, chlorodimethylsilane, dimethyl-n-propylchlorosilane, dimethylisopropylchlorosilane, t-butyldimethylchlorosilane, tripropylchlorosilane, dimethyloctylchlorosilane, tributylchlorosilane, trihexylchlorosilane, dimethylethylchlorosilane, dimethyloctadecylchlorosilane, n-butyldimethylchlorosilane, bromomethyldimethylchlorosilane, chloromethyldimethylchlorosilane, 3-chloropropyldimethylchlorosilane, dimethoxymethylchlorosilane, methylphenylchlorosilane, triethoxychlorosilane, dimethylphenylchlorosilane, methylphenylvinylchlorosilane, benzyldimethylchlorosilane, diphenylchlorosilane, diphenylmethylchlorosilane, diphenylvinylchlorosilane, tribenzylchlorosilane, and 3-cyanopropyldimethylchlorosilane. Specific examples of organic silylamines include N-trimethylsilylimidazole, N-t-butyldimethylsilylimidazole, N-dimethylethylsilylimidazole, N-dimethyl-n-propylsilylimidazole, N-dimethylisopropylsilylimidazole, N-trimethylsilyldimethylamine, N-trimethylsilyldiethylamine, N-trimethylsilylpyrrole, N-trimethylsilylpyrrolidine, N-trimethylsilylpiperidine, pentafluorophenyldimethylsilylamine and 1-cyanoethyl (diethylamino)dimethylsilane. Specific examples of organic silylamides and their derivatives include N,O-bistrimethylsilylacetamide, N,O-bistrimethylsilyltrifluoroacetamide, N-trimethylsilylacetamide, N-methyl-N-trimethylsilylacetamide, N-methyl-N-trimethylsilyltrifluoroacetamide, N-methyl-N-trimethylsilylheptafluorobutyramide, N-(t-butyldimethylsilyl)-N-trifluoroacetamide, and N,O-bis (diethylhydrosilyl)trifluoroacetamide. Specific examples of organic silazanes include hexamethyldisilazane, heptamethyldisilazane, 1,1,3,3-tetramethyldisilazane, 1,3-bis(chloromethyl)tetramethyldisilazane, 1,3-divinyl-1,1,3,3-tetramethyldisilazane and 1,3-diphenyltetramethyldisilazane. Examples of other silylating agents include N-methoxy-N,O-bistrimethylsilyltrifluoroacetamide, N-methoxy-N,O-bistrimethylsilyl carbamate, N,O-bistrimethylsilyl sulfamate, trimethylsilyl trifluoromethanesulfonate, and N,N'-bistrimethylsilyl urea. A preferred silylating agent is hexamethyldisilazane represented by the following formula:

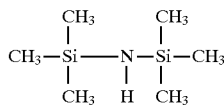

The catalyst may also be subjected to a hydration treatment before the silylation. The hydration treatment herein means to contact (before silylation) the catalyst with water and then heat the catalyst or to contact the catalyst with water vapor at a high temperature, generally 100° C. or more, preferably in the range of 150°–450° C., for 0.5–6 hours. The hydration treatment is most preferably conducted by exposing the catalyst to water vapor at a temperature of 300°–450° C. for 1–6 hours.

The catalyst thus prepared may be used in any desired physical forms, e.g., powders, flakes, spherical particles and pellets.

Oxirane compounds can be produced by reacting an organic hydroperoxide with an olefin in the presence of the catalyst prepared by the method described above.

An organic hydroperoxide is a compound having the formula

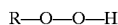

wherein R is a monovalent hydrocarbyl group. The compound reacts with an olefinic compound to form an oxirane compound and a compound R—OH.

R is preferably a group having 3–20 carbon atoms, more preferably a hydrocarbyl group and secondary or tertiary alkyl or aralkyl group, each having 3–10 carbon atoms. Particularly preferred of these groups are tertiary alkyl groups and secondary or tertiary aralkyl groups. Specific examples thereof include the tert-butyl group, tert-pentyl group, cyclopentyl group, 1-phenylethyl-1 group, 2-phenylpropyl-2 group and tetralinyl group formed by removing a hydrogen atom from the aliphatic side chain of a tetralin molecule.

Examples of aralkyl hydroperoxide having a hydroperoxy group bonded to a carbon atom present in the alkyl side chain directly bonded to the aromatic ring include ethylbenzene hydroperoxide (1-phenylethyl-1-hydroperoxide) and cumene hydroperoxide (2-phenylpropyl-2-hydroperoxide).

When ethylbenzene hydroperoxide is used, the hydroxyl compound obtained is 1-phenylethanol (methyl phenyl carbinol), which can be converted to styrene by dehydration. When cumene hydroperoxide is used, the resulting hydroxyl compound is 2-phenyl-2-propanol (dimethyl phenyl carbinol), which can be converted to α-methylstyrene by dehydration. Both styrene and α-methylstyrene are industrially useful substances.

When tert-pentyl hydroperoxide is used, resulting tert-pentyl alcohol is useful as a precursor of methyl tert-pentyl ether, which is an octane number improving agent; and tert-amylene obtained by dehydration of tert-pentyl alcohol is useful as a precursor of isoprene. When t-butyl hydroperoxide is used, resulting t-butyl alcohol is useful as a precursor of methyl t-butyl ether, which is an octane number improving agent.

The organic hydroperoxide used as the starting material may be a dilute or concentrated, purified or unpurified substance.

In general, an organic compound having at least one olefinic double bond can be reacted with an organic hydroperoxide. The organic compound may be acyclic, monocyclic, bicyclic or polycyclic and may be monolefinic, diolefinic or polyolefinic. When the compound has two or more olefinic bonds, the bonds may be either conjugated bonds or nonconjugated bonds. The compound is preferably an olefinic compound having 2–60 carbon atoms. Though the compound may have a substituent, the substituent is preferably a relatively stable group. Examples of such hydrocarbons include ethylene, propylene, butene-1, isobutylene, hexene-1, hexene-3, octene-1, decene-1, styrene and cyclohexene. Examples of the diolefinic hydrocarbons include butadiene and isoprene. The compound may have a substituent, of which an example is a halogen atom. The compound may further have various substituents which comprise an oxygen, sulfur and/or nitrogen atom together with a hydrogen and/or carbon atom. Particularly preferred olefinic compounds are olefinic unsaturated alcohols and halogen-substituted olefinic unsaturated hydrocarbons, examples of which include allyl alcohol, crotyl alcohol and allyl chloride. Particularly preferred are alkenes having 3–40 carbon atoms, which may be substituted with a hydroxyl group or halogen atom.

The usefulness of oxirane compounds has been known since long. Many oxirane compounds are useful industrial chemicals, olefin oxides such as ethylene oxide and propylene oxide being particularly important. Propylene oxide can be converted to useful polymeric products by polymerization or copolymerization. Epichlorohydrin, which is also industrially important, can be obtained from allyl chloride. If desired, epichlorohydrin can be converted to glycerol. It is also possible to produce glycerol from an oxirane compound obtained from allyl alcohol.

Oxirane compounds can be produced by use of the catalyst composition which is prepared by the method specified above and which is substantially insoluble in the epoxidation reaction mixture and hence can form a heterogeneous system. The above-mentioned catalyst composition used has a very high activity and can convert organic hydroperoxides with a high conversion and has a high selectivity to oxirane compounds. The term "selectivity" herein means the molar ratio of the oxirane compound formed to the organic hydroperoxide converted.

In general, an epoxidation reaction can be conducted in a liquid phase using a solvent and/or a diluent. The solvent and diluent are preferably those which are liquid at the temperature and pressure of the reaction and substantially inert to the reactants and the reaction products. The solvent may also be a substance which is already present in the hydroperoxide solution used. For example, when the ethylbenzene hydroperoxide (EBHPO) used is a mixture of EBHPO and ethylbenzene, which is a starting material thereof, the ethylbenzene may be substituted for solvent with no particular addition of solvent. A second solvent also may be used as the diluent. Examples of solvents useful as diluents include aromatic monocyclic compounds (e.g., benzene, toluene, chlorobenzene, bromobenzene and o-dichlorobenzene) and alkanes (e.g., octane, decane and dodecane). It is also possible to use an excessive amount of olefinic reactants as the solvent. Thus, along with the solvent supplied together with an organic hydroperoxide, an excessive amount of an olefinic reactant can be used as a solvent. The amount of the whole of the solvents used is preferably 20 mole or less per mole of hydroperoxide.

The epoxidation reaction temperature is preferably 0°–200° C., more preferably 25°–200° C. The reaction pressure should be sufficient to keep the reaction mixture in the liquid state and is preferably 100–10,000 KPa.

After completion of the epoxidation reaction, a liquid mixture containing the desired product can be easily separated from the catalyst composition. The liquid mixture can then be purified by appropriate methods. The methods of purification include fractional distillation, selective extraction, filtration, washing, etc. The solvent, catalyst, unreacted olefin and unreacted hydroperoxide can be recycled and reused.

The process of the present invention may be advantageously practiced by using the catalyst in the form of slurry or fixed bed. In a large scale commercial operation, a fixed bed is preferably used. The process of the present invention may be conducted batchwise, semi-continuously or continuously. When a liquid containing the reactants is passed through a fixed bed, the liquid mixture going out from the reaction zone contains no or substantially no catalyst.

EXAMPLES

The present invention is described in more detail with reference to Examples. It is needless to say that the invention is not limited by the Examples.

Example 1

Preparation of Catalyst

A commercially available silica gel (10–40 mesh, specific surface area 300 $m^2/g$, average pore diameter 10 nm) (50 g), tetraisopropyl titanate (2.2 g), acetylacetone (1.65 g) and isopropanol (200 ml) were mixed, then stirred at room temperature for 30 minutes, and the mixture was filtered. The solid part was immersed in isopropanol (50 ml), washed by stirring, and the liquid was removed by filtration. This operation was repeated three times. The solid part was dried under a nitrogen stream at 500° C. for 2 hours and then calcined under an air stream at 600° C. for 4 hours.

The substance (10 g) obtained by the calcining, hexamethyldisilazane (4 g) and toluene (50 g) were mixed, and then stirred with heating under pressure at 200° C. for 1 hour. The liquid was removed from the mixture by filtration. The remaining solid was washed with toluene (50 g) and dried under vacuum (120° C., 10 mmHg, 3 hours) to obtain a catalyst.

Synthesis of propylene oxide by epoxidation of propylene using ethylbenzene hydroperoxide:

The catalyst thus prepared (Ti content 0.75% by weight, as calculated on the basis of charge amounts) (2 g), 35% ethylbenzene hydroperoxide (60 g) and propylene (75 g) were placed in an autoclave and reacted at 120° C. for 1 hour. The results of the reaction are shown in Table 1.

Example 2

The same procedures as in Example 1 were repeated except that the respective amounts of tetraisopropyl titanate, acetylacetone and isopropanol were doubled to obtain a catalyst and that 1 g of the catalyst was used for the epoxidation reaction. The results of the reaction are shown in Table 1.

Example 3

The same procedures as in Example 1 were repeated except that the respective amounts of tetraisopropyl titanate, acetylacetone and isopropanol were halved to obtain a catalyst and that 4 g of the catalyst was used in the epoxidation reaction. The results of the reaction are shown in Table 1.

Comparative Example 1

The same procedures as in Example 1 were repeated except that the impregnation solvent was removed by decantation and no washing was conducted to obtain a catalyst and that 2 g of the catalyst was used in the epoxidation reaction. The results of the reaction are shown in Table 1.

Comparative Example 2

The same procedures as in Comparative Example 1 were repeated except that the respective amounts of tetraisopropyl titanate, acetylacetone and isopropanol were doubled to obtain a catalyst and that 1 g of the catalyst was used for the epoxidation reaction. The results of the reaction are shown in Table 1.

Comparative Example 3

An epoxidation reaction was carried out in the same manner as in Example 1 except that 15 mg of $TiO_2$ (titania) was used as the catalyst. The results of the reaction are shown in Table 1.

In Table 1, the higher EBHPO conversion means the higher catalyst activity; and the higher selectivity to propylene oxide and the lower selectivity to by-products (which lead to the increase of load in purification) mean the higher selectivity of catalyst. As is apparent from Table 1, the catalysts obtained by a process which, in addition to the steps of prior art processes, further comprises a washing step show increased activity and increased selectivity to intended product and decreased selectivity to by-products (compare Example 1 with Comparative Example 1 and compare Example 2 with Comparative Example 2). With regard to activity, the activity of the present catalyst is improved by 20–30% as judged from the reaction velocity ratio. Further, both of the activity and selectivity increase in the order of Examples 2, 1 and 3, wherein the Ti content decreases in this order.

TABLE

|  | Example | | | Comparative Example | | |
| --- | --- | --- | --- | --- | --- | --- |
|  | 1 | 2 | 3 | 1 | 2 | 3 |
| Ti content (wt %) | 0.75 | 1.5 | 0.38 | 0.75 | 1.5 | 60 |
| Activity |  |  |  |  |  |  |
| EBHPO conversion (%) | 99.93 | 98.22 | 99.96 | 99.62 | 96.11 | 7.80 |
| Reaction velocity ratio | 2.24 | 1.24 | 2.41 | 1.72 | 1 | 0.03 |
| Selectivity (%) |  |  |  |  |  |  |
| PO | 85.15 | 83.54 | 86.89 | 84.15 | 83.25 | 31.60 |
| PNL | 0.19 | 0.26 | 0.13 | 0.28 | 0.35 | 0.13 |
| BALD | 0.14 | 0.23 | 0.12 | 0.17 | 0.27 | 0.36 |
| PG | 0.33 | 0.32 | 0.25 | 0.36 | 0.52 | 1.72 |

Note:
EBHPO: Ethylbenzene hydroperoxide
PO: Propylene oxide
PNL: Phenol
BALD: Benzaldehyde
PG: Propylene glycol

What is claimed is:

1. A process for producing a heterogeneous catalyst used for producing an oxirane compound by reacting an olefinic compound with an organic hydroperoxide which catalyst is substantially insoluble in the reaction mixture and comprises at least one silicon compound, selected from the group consisting of silica and inorganic silicates, in chemical combination with an oxide or hydroxide of titanium, comprising:

(a) impregnating the silicon compound with a titanium compound in a solvent for impregnation, (b) removing the solvent for impregnation, (c) then washing the remaining composition with a washing solvent and removing the washing solvent, and (d) then calcining the residual composition.

2. A process according to claim 1 further including, following (d), silylating the catalyst obtained from (d).

3. A process according to claim 1 or 2, wherein the washing solvent is an alcohol.

4. A process according to claim 1 or 2, wherein the washing is carried out at from 10° to 60° C.

5. A process according to claim 1 or 2, wherein the titanium content of the catalyst is 1.5% by weight or less based on the weight of the silicon compound.

6. The process according to claim 1, wherein the solvent used for impregnation and washing is an oxygen containing organic solvent which has 1 to about 12 carbon atoms and is liquid at ordinary temperature.

* * * * *